United States Patent [19]

Garner

[11] Patent Number: 5,092,674

[45] Date of Patent: * Mar. 3, 1992

[54] MICROPIPETTE ADAPTOR FOR SPECTROPHOTOMETERS WITH TEMPERATURE CONTROL

[75] Inventor: Harold R. Garner, Encinitas, Calif.

[73] Assignee: General Atomics, San Diego, Calif.

[*] Notice: The portion of the term of this patent subsequent to Feb. 12, 2008 has been disclaimed.

[21] Appl. No.: 407,539

[22] Filed: Sep. 15, 1989

Related U.S. Application Data

[63] Continuation-in-part of Ser. No. 377,476, Jul. 10, 1989, Pat. No. 4,991,958.

[51] Int. Cl.5 .............................................. G01N 21/01
[52] U.S. Cl. ..................................... 356/244; 356/440
[58] Field of Search ....................... 336/244, 246, 440; 250/576

[56] References Cited

U.S. PATENT DOCUMENTS 3,877,817  4/1975  Ralston .............................. 356/409
4,440,497  4/1984  Carey et al. ..................... 356/318 X
4,935,875  6/1990  Shah et al. ....................... 356/319 X Primary Examiner—Vincent P. McGraw
Attorney, Agent, or Firm—Nydegger & Associates

[57] ABSTRACT

A temperature-controlled micropipette adaptor includes a metal base sandwiched between two plastic layers. The metal base has an orifice to hold a micropipette. The plastic layers hold lenses in alignment for spectrophometric measurements of a sample contained in a micropipette inserted into the orifice. A resistive heater wire is held between the metal base and the plastic layer to transfer heat from the heater wire to the metal base and thus to the micropipette sample. A thermocouple is attached to the metal layer to monitor temperature changes. A feedback control system is coupled to the device for monitoring and programmably controlling changes in temperature of the heated sample over time.

19 Claims, 3 Drawing Sheets

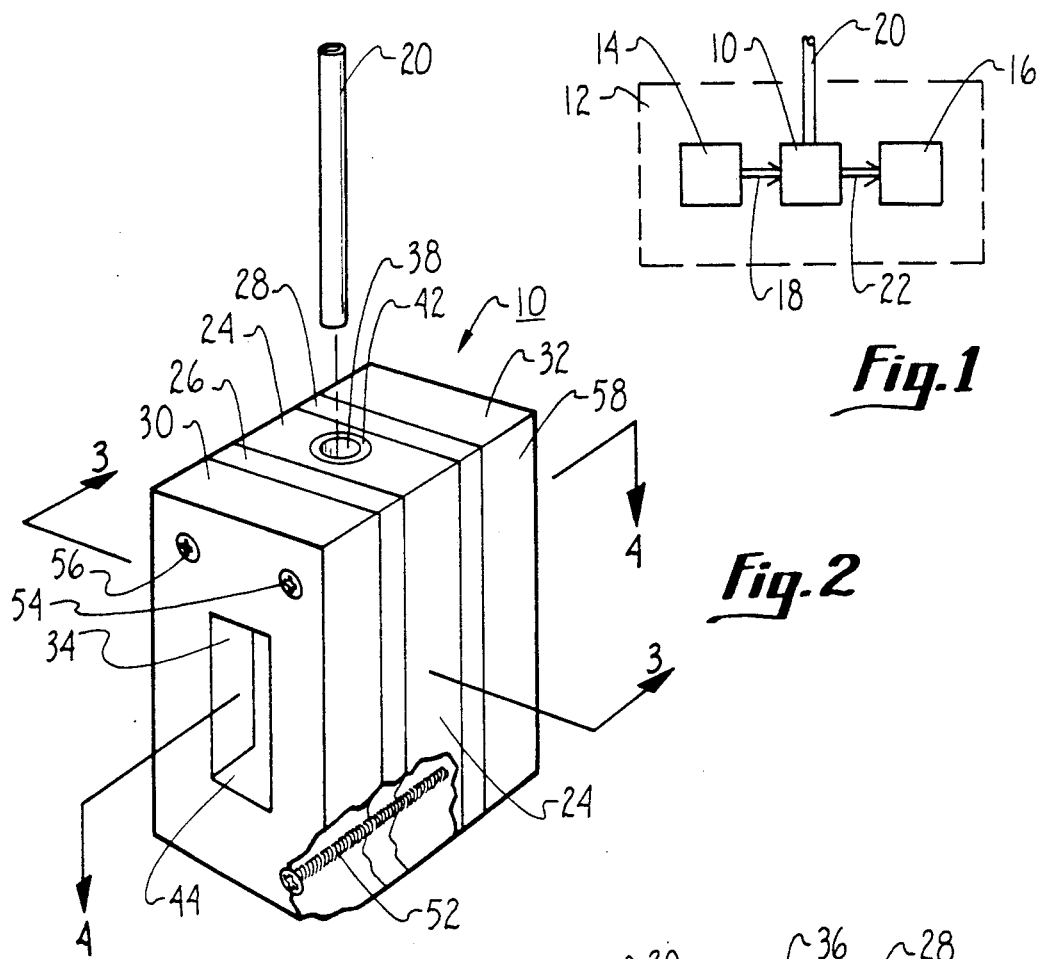

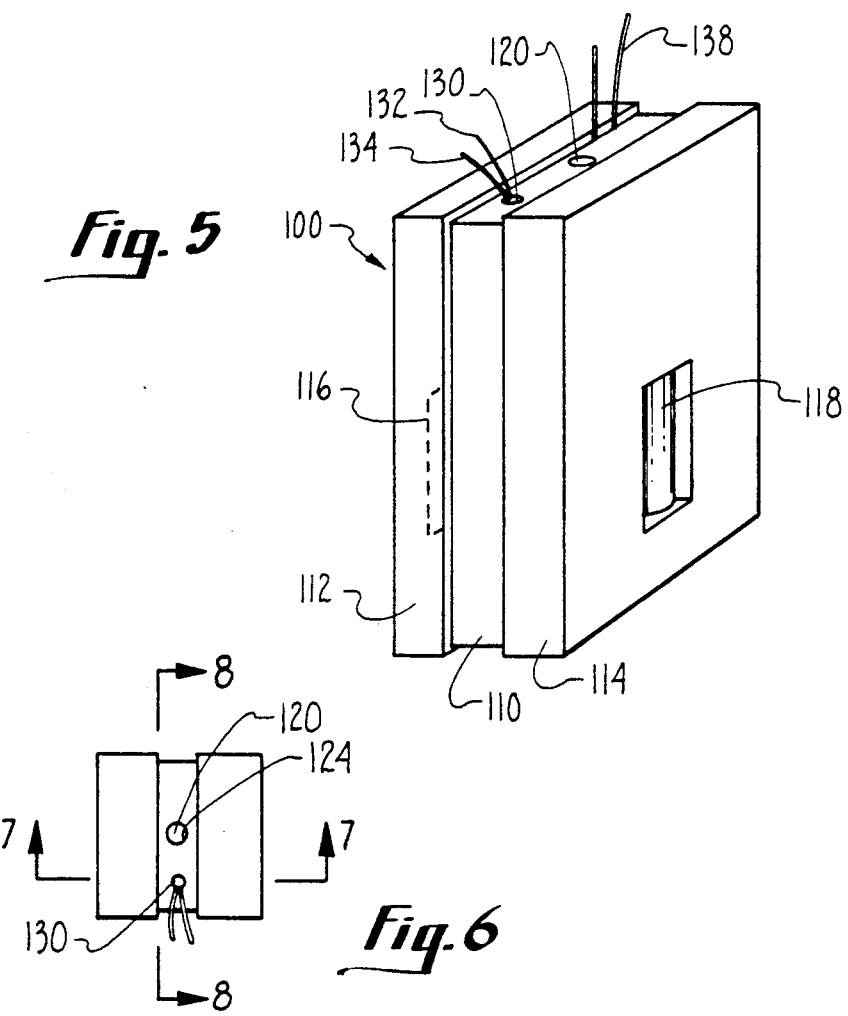
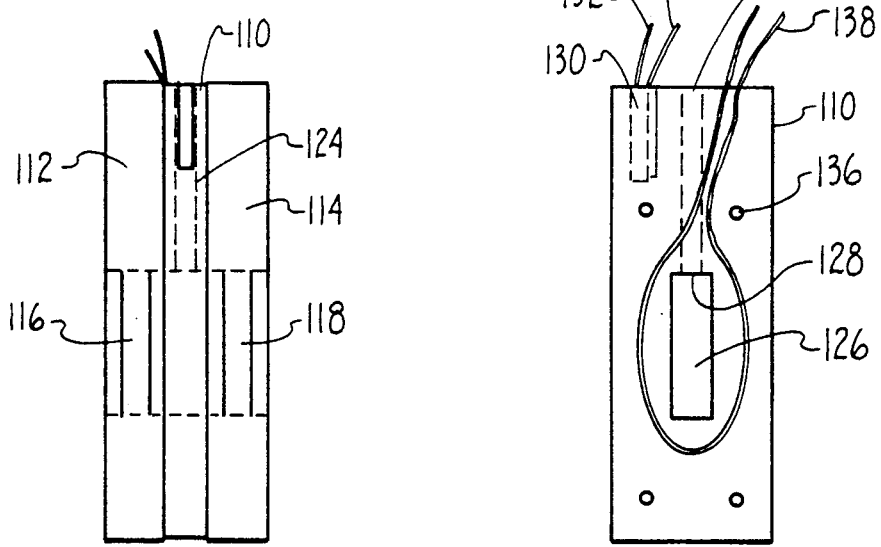

MICROPIPETTE ADAPTOR FOR SPECTROPHOTOMETERS WITH TEMPERATURE CONTROL

This application is a continuation-in-part of our prior co-pending application for a "Micropipette Adaptor for Spectrophotometers" Ser. No. 377,476 filed July 10, 1989 now U.S. Pat. No. 4,991,958.

FIELD OF THE INVENTION

The present invention pertains to devices which hold sample materials while the composition of the material is being measured and analyzed. Specifically, the present invention pertains to sample holders which may be used with spectrophotometers and colorimeters. The present invention is particularly, but not exclusively, useful for obtaining spectroscopic measurements of very small samples of material while being heated.

BACKGROUND OF THE INVENTION

The use of spectrophotometers to measure the light absorption characteristics of sample materials is well known. Indeed, the basic principles involved are relatively simple. A beam of light, whose characteristics are known, is directed through the sample material and the light that emerges is analyzed to determine which wavelengths of the original beam were absorbed, or otherwise affected, by the sample material. Based on differences between the incident light and the transmitted light, certain characteristics of the sample material can be determined. Many variables are involved, however, that can make a spectrophotometric measurement quite complex. In sum, these complexities arise from the fact that the sensitivity and accuracy of a measurement rely on the ability of the spectrophotometer to measure the light which is absorbed by the samples.

Analytically, a spectrophotometric analysis relies on a known relationship of the variables involved. Specifically, in a standard spectrophotometric measurement, the amount of light transmitted through a test cuvette is measured and the percent of transmitted light is related to the material in the cuvette by the following relationship:

$$I_t(\lambda) = I_o(\lambda) 10^{-OD}$$

where $I_o(\lambda)$ and $I_t(\lambda)$ are respectively the input and transmitted intensities, and the optical density, OD, is given by:

$$OD = \alpha(\lambda) L\ C$$

where $\alpha(\lambda)$ is the absorptivity of the material as a function of $\lambda$, L is the optical path length, and C is the concentration. From the above, it will be easily appreciated that the output intensity $I_t(\lambda)$ is directly proportional to the input intensity $I_o(\lambda)$. Therefore, it is clearly necessary to have an input intensity that is sufficient to give an output intensity which can be effectively used for analysis and measurement of the sample material. Further, the efficacy of the measurement will also be enhanced if the concentration of the sample material is increased. Thus, for spectrophotometric analysis it is desirable to have a light input of high intensity, and have a highly concentrated sample in solution. There is a problem, however, when low concentration solutions of sample material are available in only very small quantities (e.g. 0.5 to 50 micrograms/microliter).

To be effective for spectroscopic measurements, test cuvettes for holding the sample material must be completely filled. This typically requires a substantial amount of sample material. Consequently, when only a small amount of the sample material is effectively available for testing, presently available test cuvettes (e.g. 12.5 mm × 12.5 mm cuvette) are inadequate because of their relatively large size. Merely reducing the size of the cuvette is not the answer. This is so because, with a size reduction of the cuvette there is also a reduction in the amount of sample material through which light can pass. Consequently, the intensity of the light passing through the sample material is reduced and the sensitivity and accuracy of the measurement is compromised.

The present invention recognizes that it is possible to take spectrophotometric measurements of very small quantities of a sample material, even where there is a relatively low concentration of the material in solution. The present invention recognizes that this can be done by properly focusing collimated light onto the sample material to obtain sufficiently high input light intensities for the desired measurements. Further, the present invention recognizes that this focusing can be accomplished by a device which is engageable, and operatively compatible, with presently available spectrophometers such as a UVIKON Model 820 spectrophotometer by Kontron.

The present invention further recognizes that occasionally it is important to make spectroscopic observations of small samples at various controlled elevated temperatures. For example, for DNA material, it is known that the double strands of DNA break into two single strands (denatures) at temperatures above 70° C. This denaturing of the DNA is also known to result in a significant increase in the light absorption of the sample. It is desirable to spectroscopically monitor denaturization. It is also desirable to spectroscopically monitor enzymatic and other thermally-induced reactions in small biological, as well as nonbiological, samples. For example, the progress of the polymerase chain reaction of assembling DNA segments can be studied if the sample is properly heated. Indeed, part of this study requires heating the DNA sample to raise the temperature above the denaturing temperature and then reducing the temperature to allow the single strands to find their complementary sites to form new double strands.

The present invention further recognizes that it is possible to monitor spectrophotometric changes at biologically significant temperatures. Study of bacteria or virus growth at human body temperatures of 37° C. could also be possible. In addition, nonbiological chemical reactions at temperatures elevated above room temperature can also be studied. The present invention accomplishes this by providing an apparatus which allows heating of the very small quantities of sample material in a controlled and efficient manner.

In light of the above, it is an object of the present invention to provide a micropipette adaptor for spectrophotometers which allows for spectrophotometric measurements of very small quantities of sample material in solution. Another object of the present invention is to provide a micropipette adaptor for spectrophotometers which permits recovery of the sample material after spectrophotometric measurements have been made. Yet another object of the present invention is to provide a micropipette adaptor for spectrophotometers which allows spectroscopic measurements of samples while the sample is in the process of being transferred through a micropipette. Still another object of the present invention is to provide a micropipette adaptor for spectrophotometers which provides for a high light collection efficiency to increase the sensitivity of the measurements which are made. Another object of the present invention is to provide a micropipette adaptor for spectrophotometers which allows a micropipette or other capillary sample holder to be easily installed and removed from the adaptor. Yet another object of the present invention is to provide a micropipette adaptor for spectrophotometers which provides approximately the same intensity light path length product for small samples as is provided for larger samples. Another object of the present invention is to provide a micropipette adaptor for spectrophotometers which is relatively easy to manufacture and comparatively cost-effective to operate.

Further, an object of the present invention is to provide a micropipette adaptor in which the temperature of the sample may be controlled. Another object of the present invention is to provide such a temperature-controlled micropipette adaptor which may be used in commercially available spectrophometers. Yet another object of the present invention is to provide a temperature-controlled micropipette adaptor capable of easily attaining higher sample temperatures, and capable of maintaining predetermined temperatures for desired lengths of time. Another object of the present invention is to provide a temperature-controlled micropipette adaptor which is relatively simple and convenient to manufacture and use.

SUMMARY OF THE INVENTION

The micropipette adaptor for spectrophotometers according to the present invention comprises a base member which is adapted to hold a capillary tube, such as a micropipette, which is filled with a solution of the sample material to be analyzed. More specifically, the base member is formed with an opening, and is formed with a hole which is distanced across the opening from a conical well. As formed on the base member, both the hole and the conical well are aligned with each other to respectively receive a portion of the micropipette and hold it on the base member. When so held, the micropipette extends across the opening of the base member to permit light to pass through the micropipette.

An optical system is provided for the adaptor and is attached to the base member to both focus a beam of collimated light onto the micropipette, and to recollimate the light that has passed through the micropipette. For focusing the beam of collimated light, a cylindrical quartz lens (i.e. a directing lens) is positioned between the base member and the source of collimated visual or ultraviolet light. Specifically, this directing lens is used to focus collimated light from the light source into a line. In accordance with the present invention, this linearly focused light is aligned along the longitudinal axis of the micropipette to provide a very high intensity light input for the sample material which fills the lumen of the micropipette. Another cylindrical quartz lens (i.e. a receiving lens) is positioned behind the base member to receive the light which has passed through the sample material in the pipette and to recollimate it for analysis and measurement by a detector.

As contemplated by the present invention, both the directing lens and the receiving lens are respectively held by holders which are positioned on opposite sides of the base member. Importantly, each of these holders is independently adjustable in its position relative to the base member. Thus, the directing lens may be independently moved relative to the micropipette to achieve alignment of its linearly focused light with the axis of the micropipette. Similarly, the receiving lens may be moved relative to the micropipette to achieve effective recollimation of the light that has passed through the micropipette. This recollimated light is then received by a detector in the spectrophotometer for further spectroanalysis. It will be appreciated by the skilled artisan that, depending on the wavelength of the light, the receiving lens and the directing lens may be made of quartz, glass, sapphire, fused silicon or any other appropriate light transmitting material.

The temperature control feature of the micropipette adaptor includes a metal base member sandwiched between two plastic material layers. The metal base member has an orifice adapted to hold a micropipette containing a sample material solution for analysis. The plastic material layers each have a lens mounted on either side of a passageway in the center of the base member, which forms the optical system to focus the collimated light through the sample in the micropipette. A resistive heater wire is held between the metal base and one of plastic layers, in position against the surface of the metal base, to transfer heat from the heater wire to the metal base. The metal base includes a thermocouple which provides a signal representative of the temperature of the metal base, which allows the temperature of the sample material to be monitored. The micropipette of sample material is inserted into the orifice of the metal base and heated to a desired temperature. The metal base acts as a thermal reservoir for heating the sample, in addition to maintaining the alignment between the micropipette sample and the focusing lens. By choosing a base material of high thermal conductivity, such as copper, brass, or aluminum, the temperature of the sample in the micropipette can be increased quickly and maintained at a desired level.

The micropipette adaptor further includes a temperature feedback control system to maintain the sample at any desired temperature. The control system comprises an analog thermocouple gauge display driver, a digital panel meter, a comparator, a set point programmer, and a transistor heater driver. Also provided is an external input to allow programming of desired temperature variations over time.

As contemplated by the present invention, the adaptor is intended for use with very small micropipettes. For example, it is within the contemplation of the present invention that a micropipette having a capillary tube with a lumen which is approximately half a millimeter (0.5 mm) in diameter can be effectively used with the adaptor disclosed herein. Even so, it will be appreciated by the skilled artisan that pipettes of various sizes may be used. Furthermore, it is to be appreciated that the light wavelengths which are useful with the adaptor of the present invention need not necessarily be limited to the visual and ultraviolet ranges.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a schematic diagram showing the micropipette adaptor in its operative relationship with elements of a spectrophotometer;

FIG. 2 is a perspective view of the micropipette adaptor with selected elements shown in phantom and portions broken away for clarity;

FIG. 3 is a cross-sectional view of the micropipette adaptor as seen along the line 3—3 in FIG. 2;

FIG. 4 is a cross-sectional view of the micropipette adaptor as seen along the line 4—4 in FIG. 2;

FIG. 5 is a perspective view of a micropipette adaptor having temperature control in accordance with the present invention;

FIG. 6 is a top view of the adaptor with temperature control of FIG. 5;

FIG. 7 is a cross-sectional view of the adaptor with temperature control as seen along line 7—7 of FIG. 6;

FIG. 8 is a cross-sectional view of the adaptor with temperature control as seen along the line 8—8 of FIG. 6.

DESCRIPTION OF THE PREFERRED EMBODIMENT

Figure 9:
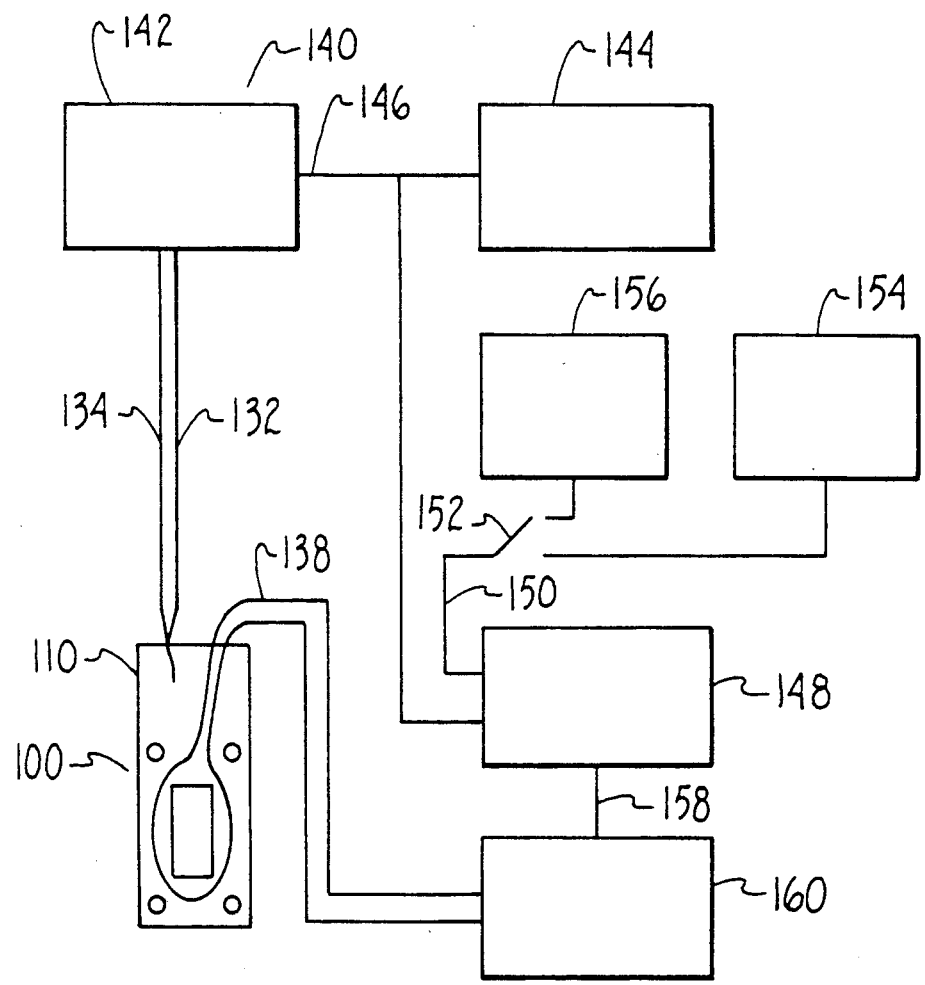
FIG. 9 is a schematic diagram of a feedback control system used in conjunction with the adaptor of FIG. 5 in accordance with the present invention.

Referring initially to FIG. 1, the micropipette adaptor for spectrophotometers in accordance with the present invention is schematically shown in its operative environment and is designated 10. As shown, adaptor 10 is positioned for operative engagement with a spectrophotometer 12 and, specifically, is positioned between a light source 14 and a detector 16. As so positioned, an input beam of collimated light 18, having an intensity $I_o(\lambda)$, is directed from the light source 14 toward the adaptor 10. In a manner to be subsequently disclosed, adaptor 10 focuses the beam 18 of collimated light onto a micropipette 20 which is held by the adaptor 10. Adaptor 10 then recollimates this light into an output light beam 22 which has an intensity of $I_f(\lambda)$. As will be appreciated by the skilled artisan, the difference between $I_o(\lambda)$ and $I_f(\lambda)$ is indicative of the light absorption characteristics of the sample material held in micropipette 22 and, hence, is an indication of the composition of the sample material.

The construction of adaptor 10 will, perhaps, be best seen by reference to FIG. 2 wherein it is shown that adaptor 10 comprises a base member 24 which is sandwiched between a resilient member 26 and a resilient member 28. Respectively positioned against resilient members 26 and 28 and opposite base member 24 are holders 30 and 32. Preferably, base member 24 and the holders 30 and 32 are made of a rigid material, such as black delrin plastic, while the resilient members 26 and 28 are made of an elastomeric material such as rubber or foam plastic. For purposes of the present invention, holder 30 is formed with an opening 34 as shown in FIG. 2, and base member 24, resilient members 26, 28 and holder 32 are each formed with openings (not shown in FIG. 2) which are aligned with opening 34 to establish a pathway 44 which allows light to pass through adaptor 10.

Referring now to FIG. 3, it will be seen that base member 24 is formed with an opening 36 which, as indicated above, is positioned in alignment with opening 34 of holder 30. Further, base member 24 is shown formed with a hole 38 and a conical-shaped well 40 which are positioned across the opening 36 from each other. Specifically, hole 38 and conical well 40 respectively receive portion of micropipette 20 to hold the micropipette 20 in place within and across the opening 36. A bushing 42, which is appropriately sized to receive micropipette 20, may be positioned in hole 38 to securely hold the micropipette on adaptor 10.

As best seen in FIG. 4, the base member 24, together with its adjacent resilient members 26, 28 and the holders 30, 32 are all positioned with their respective openings aligned to create a pathway 44 through adaptor 10 along which light can shine. FIG. 4 also shows that a lens 46 is positioned in pathway 44. Specifically, lens 46 is attached or mounted on holder 30 by any means well known in the pertinent art, such as by gluing or solvent bonding. Further, lens 46 may be mounted on holder 30 by a frictional snap-in configuration or held thereon by set screws (not shown). Similarly, a lens 48 is attached or mounted on holder 32 and is positioned in the pathway 44 substantially as shown. For purposes of the present invention, it is preferable that the lenses 46, 48 be cylindrical. This is so in order for the lens 46 (the directing lens) to linearly focus input light beam 18 onto a line which can be positioned along the longitudinal axis of micropipette 20. Further, a cylindrical shape for lens 48 (the receiving lens) is also preferable in order for the linearly focused input light beam 18 to be recollimated as output light beam 22. Preferably, both cylindrical lens 46 and cylindrical lens 48 are made of a quartz material which permits use of either visible or ultraviolet light.

As will be appreciated by the skilled artisan, input light beam 18 can be precisely focused along the longitudinal axis of micropipette 20 by appropriately moving lens 46 in a direction along the pathway 44. In order to linearly focus input light beam 18 and obtain the highest intensity $I_o(\lambda)$ for the light which is incident on the sample material being held in micropipette 20, the holder 30 on which lens 46 is mounted, can be moved relative to the base member 24 on which micropipette 20 is mounted. As seen in FIG. 4, when lens 46 is properly positioned, input beam 18 will be focused into a line which is coincident with the center of lumen 50 of micropipette 20. Following well known optical principles, light will emerge from micropipette 20 in a predictable fashion. Consequently, cylindrical lens 48 (the receiving lens) can receive this emerging light and recollimate the light into the output light beam 22. To accomplish this, lens 48 is mounted on holder 32 and is movable therewith relative to base member 24. As will be readily appreciated, the resilient members 26, 28 permit selective relative movement between base member 24 and the respective holders 30, 32. At the same time, resilient members 26, 28 provide a support for maintaining the relative positions of these components when they are not being moved. It is possible, however, to completely eliminate the resilient members 26, 28. Manufacturing tolerances may suffice to properly position lens 46 on holder 30 without any further adjustment necessary to predictably focus light from the lens 46 along the interior lumen of micropipette 20. Similarly, lens 48 may be mounted on holder 32 and positioned relative to base member 24 without the need for subsequent adjustments.

The mechanism for moving holders 30, 32 relative to base member 24 will be best seen by referring to FIG. 2 wherein a screw 52 is shown extending through holder 30 and resilient member 26 for threadable connection with base member 24. The screws 54 and 56 likewise connect holder 30 with base member 24. Similarly, screws (of which the screw 58 shown in phantom is exemplary) connect holder 32 with base member 24. In each case, the screws 52, 54, 56, 58 (and others not shown) can be individually rotated to independently move the holders 30, 32 relative to the base member 24. Consequently, this moves lenses 46, 48 relative to micropipette 20.

As intended for the present invention, movement of cylindrical lens 46 relative to micropipette 20 is accomplished to linearly focus input light beam 18 along the axis of micropipette 20. This increases the intensity $I_o(\lambda)$ of the light which is incident on the sample material held in solution in lumen 50 of micropipette 20. Similarly, movement of the cylindrical lens 48 relative to micropipette 20 is accomplished in order to recollimate the light which emerges from micropipette 20 for easier analysis of its intensity $I_t(\lambda)$ by the detector 16.

Referring now to the embodiment of a micropipette adaptor as shown in FIGS. 5-9, there is shown an adaptor with temperature control which is generally designated 100. The adaptor 100 can generally be thought of as being used in place of adaptor 10 earlier described. In particular, adaptor 100 comprises a base member 110 sandwiched between a layer 112 and a layer 114. Base member 110 is made of a metal material which has high thermal conductivity and is easy to machine, such as copper, brass or aluminum. Layers 112, 114 are made of a different material, preferably nonmetal, such as delrin plastic, which are attached, such as by bonding, to each side of base member 110. The overall dimensions of the adaptor are such that it easily fits into a conventional sample holder slot of a commercially available spectrophotometer. In the embodiment shown, the dimensions of layers 112 and 114 are approximately 12.5 millimeters in width, and approximately 38 millimeters in height. Base member 110 is slightly smaller in these dimensions, i.e. width and height, to prevent heat loss by contact of the base member 110 with the spectrophotometer. Lenses 116 and 118 are mounted in layers 112, 114 respectively, similar to mounting of lenses 46, 48 as earlier shown in FIG. 4.

Base member 110 has an orifice 120 in the top thereof. Orifice 120 is generally cylindrical and vertically oriented in base member 110 for receiving a micropipette containing sample material. Orifice 120 has a top 122 and walls 124 adapted to the shape of the micropipette. Base member 110 has a passageway 126, into which orifice 120 opens at orifice bottom 128. A micropipette which is inserted into orifice 120 then may extend through orifice 120 down into passageway 126. Then a collimated light beam, such as light beam 18 of FIG. 4, can be passed through the sample. Base member 110 further includes a thermocouple 130 for measuring the temperature of base member 110. Thermocouple 130 is preferably a chromel-alumel thermocouple having wires 132, 134, which provide a temperature signal.

Quartz lenses 118, 116 may be held in place with teflon tipped set screws inserted into set screw slots 136. A heater wire 138 is positioned and held between layer 112 and base member 110. It is routed around the perimeter of passageway 126 and is positioned against base member 110 being held firmly in place by layer 112. Heater wire 138 is preferably made of manganin, five thousandths (0.005) inches in diameter. It will be appreciated, however, that tungsten or other resistive type wires are also appropriate for use as heater wire 138. Wire 138 is connected to a direct current power supply (not shown) for heating the wire, with typical values for the output of the supply being from five tenths to one (0.5-1.0) amperes at two to four (2-4) volts.

Thus, the adaptor 100 serves at least two functions, namely maintaining the alignment between the sample and the focusing lenses, and further acting as a thermal reservoir. By applying the proper amount of voltage and power levels to heater wire 138, the base member 110 can be heated. This results in heating of the sample which is contained in a micropipette inserted in orifice 120 to the desired temperature. It has been found, for example, that use of four (4) watts of power may be used to obtain temperatures of a micropipette sample of eighty to one hundred degrees (80°-100° C).

There is further shown in FIG. 9 a feedback control system generally indicated as 140 for operably controlling the temperature of adaptor 100. In particular, system 140 comprises a thermocouple circuit 142 connected to thermocouple outputs 132, 134 from base member 110. The temperature output of thermocouple circuit 142 may be displayed by digital panel meter 144. In addition, output 146 of thermocouple circuit 142 is connected to a comparator 148. Also connected as an input to comparator 148 is a set point input signal line 150. The actual measured thermocouple output signal 146 is compared to the set point 150 at comparator 148. Set point signal information 150 can be alternately provided via switch 152 between a signal generated by a temperature set point potentiometer 154, or a signal generated by an analog temperature programming input device 156. Potentiometer 154 can be set by selecting a desired voltage which corresponds to the desired temperature at which the base member is to be maintained. On the other hand, the temperature programming input 156 provides an external input to provide a varying time/temperature wave form using an analog signal. Thus, the set point signal 150 can be programmed to maintain a constant temperature based on the potentiometer 154 setting, or specific temperatures for predetermined periods of time based on the programming input 156. Based upon the comparison between the set point signal 150 and the actual measured temperature signal 146, the comparator generates an "on" or "off" signal 158. This activates or deactivates a transistor heater driver 160. Driver 160 sends a current through heater wire 138 to heat up base member 110 when it is activated, or cuts off the current to allow base member 110 to cool down when it is deactivated.

In one experiment utilizing adaptor 100, the absorption of light at 260 nanometers of DNA was observed and measured as it was being denatured at a temperature of between seventy and eighty degrees centigrade (70°-80° C.). Since double-stranded DNA denatures at these temperatures, it was found that the absorption at 260 nanometers increased by approximately thirty-seven percent (37%). The melting temperature, or denaturing temperature, is approximately eighty-three degrees (83°). Thus, by ramping the temperature rapidly by applying one ampere to the adaptor 100, the temperature was allowed to ramp upward after reaching seventy degrees centigrade (70° C.), which is the temperature at which DNA should begin to denature. Using the adaptor 100 of the present invention took approximately ten minutes to reach eighty degrees centigrade (80° C.) from twenty-three degrees centigrade (23° C.). The absorbance of the sample used, namely Lambda DNA markers, at a concentration of 675 micrograms per milliter, changed from 0.589 before denaturing to 0.737 after denaturing, or changed approximately twenty-five percent (25%). Thus, the usefulness of the present invention can readily be appreciated by those skilled in the art.

While the particular micropipette adaptor for spectrophotometers with temperature control as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An adaptor for holding a micropipette in a spectrophotometer having a source of collimated light and a detector, comprising:
   a first layer and a second layer;
   a metal base member adapted to hold said micropipette, said base member being positioned between and attached to said first and second layers;
   a heater wire in direct contact with said base member for heating said base member holding said micropipette; and
   means for monitoring the temperature of said base member.

2. An adaptor for holding a micropipette in a spectrophotometer having a source of collimated light and a detector as recited in claim 1, further comprising feedback control means coupled to said heater wire and said monitoring means for maintaining said base member at a preselected temperature for a preselected interval of time.

3. An adaptor for holding a micropipette in a spectrophotometer having a source of collimated light and a detector as recited in claim 2, wherein said monitoring means is a chromel-alumel thermocouple.

4. An adaptor for holding a micropipette in a spectrophotometer having a source of collimated light and a detector as recited in claim 1, wherein said metal base member is made of copper, aluminum, or brass.

5. An adaptor for holding a micropipette in a spectrophotometer having a source of collimated light and a detector as recited in claim 1, wherein said first and second layers comprise a plastic material.

6. An adaptor for holding a micropipette in a spectrophotometer having a source of collimated light and a detector as recited in claim 1, wherein said heater wire is coated manganin wire positioned between said base member and one of said layers.

7. An adaptor for holding a micropipette in a spectrophotometer having a source of collimated light and a detector as recited in claim 6, wherein said base member has a passageway therethrough and wherein said heater wire is routed around said passageway.

8. An apparatus for analyzing a sample solution contained in a micropipette, comprising:
   means for receiving a source of collimated light to linearly focus said light;
   a metal base for holding said micropipette in axial alignment with said linearly focused light;
   means for receiving and recollimating said focused light which has passed through said micropipette; and
   means for heating said metal base for heating a sample solution contained in the micropipette which is held in said metal base.

9. An apparatus for analyzing a sample solution contained in a micropipette as recited in claim 8 wherein said heating means comprises a heater wire connected to said metal base.

10. An apparatus for analyzing a sample solution contained in a micropipette as recited in claim 9, further comprising a thermocouple connected to said metal base for providing an actual measured temperature signal.

11. An apparatus for analyzing a sample solution contained in a micropipette as recited in claim 10, further comprising a feedback control system connected to said wire and thermocouple for maintaining said metal base at a preselected temperature for a preselected period of time.

12. An apparatus for analyzing a sample solution contained in a micropipette as recited in claim 10, wherein said control system includes means for providing a temperature set point, and a comparator for comparing said set point to said actual measured signal.

13. An apparatus for analyzing a sample solution contained in a micropipette as recited in claim 12, wherein said comparator is coupled to a transistor heater driver for heating said wire in response to said actual measured temperature being less than said set point.

14. A method for analyzing a sample solution contained in a micropipette, comprising the steps of:
   receiving a source of collimated light to linearly focus said light;
   holding said micropipette in a metal base in axial alignment with said linearly focused light;
   receiving and recollimating said focused light which has passed through said micropipette; and
   heating said metal base to heat a sample solution contained in the micropipette which is held in said metal base.

15. A method for analyzing a sample solution contained in a micropipette as recited in claim 14, further comprising the step of measuring the temperature of said metal base.

16. A method for analyzing a sample solution contained in a micropipette as recited in claim 15, further comprising the step of comparing said measured temperature to a set point temperature, and heating said metal base when said set point temperature exceeds said measured temperature.

17. A method for analyzing a sample solution contained in a micropipette as recited in claim 16, further comprising the step of maintaining said sample at a preselected elevated temperature for a preselected interval of time.

18. A method for analyzing a sample solution contained in a micropipette as recited in claim 17, further comprising the step of sandwiching said metal base between a first and second layer of plastic.

19. An adaptor for holding a micropipette in a spectrophotometer having a source of collimated light and a detector, comprising:
   a continuous laminate comprising a first layer, a second layer, and a metal base member sandwiched therebetween, said base member adapted to hold said micropipette;
   a continuous light passageway formed through said laminate and positioned to provide light communication between said source of light and said detector through said laminate and said micropipette held therein;
   a heater wire connected to said base member for heating said base member holding said micropipette; and
   means for monitoring the temperature of said base member.

* * * * *